(12) United States Patent
Oron et al.

(10) Patent No.: US 7,389,024 B2
(45) Date of Patent: Jun. 17, 2008

(54) OPTICAL HOT TIP (75) Inventors: Ram Oron, Rehovot (IL); Doron Nevo, Ra'anana (IL); Moshe Oron, Rehovot (IL)

(73) Assignee: KiloLambda Technologies Ltd. (IL)

( * ) Notice: Subject to any disclaimer, the term of this patent is extended or adjusted under 35 U.S.C. 154(b) by 0 days.

(21) Appl. No.: 10/574,974

(22) PCT Filed: Oct. 8, 2004

(86) PCT No.: PCT/IB2004/003289

§ 371 (c)(1),
(2), (4) Date: Apr. 7, 2006

(87) PCT Pub. No.: WO2005/036210

PCT Pub. Date: Apr. 21, 2005

(65) Prior Publication Data

US 2007/0127870 A1    Jun. 7, 2007

Related U.S. Application Data (60) Provisional application No. 60/510,046, filed on Oct. 9, 2003.

(51) Int. Cl.
*G02B 6/42* (2006.01)
(52) U.S. Cl. .......................... 385/38; 385/139
(58) Field of Classification Search .............. 385/5, 385/27–28, 31, 38, 76–78, 88–89, 92, 94, 385/96–99, 123–128, 139–141
See application file for complete search history.

(56) References Cited

U.S. PATENT DOCUMENTS

| 3,891,302 | A |   | 6/1975  | Dabby et al. ............ 350/96 |
|-----------|---|---|---------|--------------------------------|
| 3,914,464 | A |   | 10/1975 | Thomasson et al. ....... 427/54 |
| 4,732,449 | A |   | 3/1988  | Fan ...................... 350/96.18 |
| 4,733,931 | A |   | 3/1988  | Fan ...................... 350/96.18 |
| 5,341,238 | A |   | 8/1994  | Trost et al. ............. 359/359 |
| 5,415,655 | A |   | 5/1995  | Fuller et al. |
| 5,530,780 | A | * | 6/1996  | Ohsawa .................... 385/31 |
| 5,534,000 | A | * | 7/1996  | Bruce ...................... 606/15 |
| 5,619,600 | A |   | 4/1997  | Pohl ........................ 385/15 |
| 5,689,595 | A |   | 11/1997 | Pan ......................... 385/27 |
| 6,181,848 | B1|   | 1/2001  | Bruno et al. ............. 385/24 |
| 6,466,707 | B1|   | 10/2002 | Dawes et al. ............. 385/14 |
| 6,487,339 | B2|   | 11/2002 | Nishikawa ................. 385/32 |
| 7,099,552 | B1| * | 8/2006  | Oron et al. .............. 385/139 |
| 2002/0186921 | A1 |   | 12/2002 | Schumacher et al. |
| 2005/0135772 | A1 | * | 6/2005  | Nield et al. .............. 385/140 |

FOREIGN PATENT DOCUMENTS

EP        399660  A1  *  11/1990

OTHER PUBLICATIONS

Definition of Scattering, wordnet.princeton.edu/perl/webwn, printed Jun. 27, 2007.*

(Continued)

*Primary Examiner*—Quyen P Leung
(74) *Attorney, Agent, or Firm*—Nixon Peabody LLP (57) ABSTRACT An optical hot tip and method for manufacturing the same. The hot tip is for conducting high optical power beams at the tip of a fiber or waveguide. The light from the fiber or waveguide is absorbed in and end tip in order to generate heat. The heat can then be used in a variety of applications.

26 Claims, 7 Drawing Sheets

OTHER PUBLICATIONS

Definition of Diffusion, en.wikipedia.org/wiki/diffusion, printed Jun. 27, 2007.*

PCT Publication No. WO 2005/036210 A2, published Apr. 21, 2005.

* cited by examiner

OPTICAL HOT TIP

CROSS-REFERENCE TO RELATED APPLICATION

This application claims priority to U.S. Provisional Application No. 60/510,046, filed on Oct. 9, 2003.

FIELD OF THE INVENTION

The present invention relates to fiber or waveguide optical hot tip devices and methods of producing such devices, and particularly to such devices and methods for all-optical creation of high temperatures at a tip having a small absorbing volume.

BACKGROUND OF THE INVENTION

Fiber lasers today are capable of supplying powers of a few watts, and feed an end piece that can be heated by the optical power to temperatures of a few hundred or even more than a thousand degrees Celsius. These hot end pieces or "hot tips" are useful in, e.g., medical local heating, fuel ignition and ammunition detonation, where high, concentrated heat fluxes are needed.

Two kinds of end pieces are of interest: the first being heating by conduction from the hot surface, and the second being heating the media surrounding the hot tip via light scattering from the hot tip and absorption by the surrounding media.

The hot tips should be capable of handling high powers without being damaged and of being operated by a wide spectral range of lasers of various kinds.

SUMMARY OF THE INVENTION

It is therefore a broad object of the present invention to provide high-damage-threshold, high-temperature hot tips.

It is a further object of the present invention to provide a hot tip for use at the tip of a waveguide or optical fiber system, where the creation of the hot tip can be executed using optical means or optical laser radiation, enabling creation of the hot tip inside a waveguide assembly (in situ) after the waveguide and all other components are already manufactured.

It is still a further object of the present invention to provide hot tips for use in a waveguide or optical fiber, the hot tips operating in a broad range of wavelengths.

It is still another object of the present invention to provide hot tips for use in a waveguide or optical fiber, where the core or central portion of the hot tip scatters the light impinging on it, and the absorption is at a heat sink covering the fiber core and clad area, enabling high-power operation without extreme heating of the core of the optical fiber or waveguide part.

In accordance with the invention, there is therefore provided an optical hot tip device comprising a waveguide having an input end leading to a scattering core or scattering central area, having an absorbing, larger-area, outer heat sink.

In accordance with the invention, there is therefore provided an additional optical hot tip device comprising a waveguide having an input end leading to a scattering and absorbing nano-structure, where the scattered light impinges on absorbing particles, creating a hot disc at the waveguide tip.

Several methods for preparation and design will be described. In certain of the designs the light is scattered and absorbed at the tip or far end of the fiber or waveguide, while other designs lead to a hot cylinder at the end of the fiber or waveguide.

The following advantages can be realized:

a. Hot tips that are broadband and can be applied to all light bands, e.g., at regions of 0.8, 1.3 and 1.5 micrometers, and can serve as hot tips for a multitude of different light sources at the same time.

b. Hot tips have very high damage thresholds and can withstand high input powers for long periods of time.

c. Power dissipation is in a small volume heat sink, permitting high temperatures to be sustained.

d. The designs can be applied to single-mode, multi-mode and polarization-maintaining fibers as well as waveguides having similar properties.

e. The creation of the hot tip is based on production by an external laser light, simplifying the creation process.

The scattering inner core can be produced by the "Fiber Fuse" method (Method A), producing a relatively long scatterer, or the "Laser Plasma" method (Method B), producing a short scatterer.

The "Fiber Fuse" Method for Scattering Inner Core Manufacturing (Method A)

The "Fiber Fuse" is a phenomenon that results in the destruction of an optical fiber core, creating a string of empty bubbles in the core, which are highly scattering.

"Fiber Fuse" has been observed at laser powers on the order of $3 \times 10^6$ watts/cm2 in the core. The "Fiber Fuse" is characterized by the propagation of a bright visible light from the point of initiation toward the laser source. The term "Fiber Fuse" has been adopted for the phenomenon because of the similarity in appearance to a burning fuse. The "Fiber Fuse" has been shown to occur when the end of the fiber is contaminated, and it has also been initiated spontaneously from splices and in-core fiber gratings. Examination of the fiber core after the "Fiber Fuse" passes reveals extensive damage. The silica core is melted and re-fused, and bubbles are formed throughout its length. The damage regions, or bubbles, observed in the core after "Fiber Fuse" propagation, have been the subject of investigations. Atomic force microscope tests show that the bubbles are hollow, indicating vaporization of the silica The structure of the bubbles is in many cases a periodic structure. The "Fiber Fuse" phenomenon is used here to create scattering, or change of direction of the impinging light by the bubbles, in terminators, thus creating an angularly spread light source at the terminator, that does not reflect the light back into the input fiber but into the cladding and the absorbers surrounding the cladding.

The "Fiber Fuse" is readily initiated in most fibers. It appears as a brilliant white visible spot that propagates from the point of initiation at the fiber end toward the laser source. The spectrum of the light emitted from the fuse corresponds approximately to a temperature of 5400 oK, indicating that the "Fiber Fuse" may consist of plasma. The speed of the "Fiber Fuse" propagation is about 1 meter per second in most fibers. The "Fiber Fuse" can travel through many meters of fiber. The fiber gets non-transparent and scattering, thus serving as a good scatterer for high-power terminators.

The high-energy laser light (e.g., providing 30-35 dBm CW power at 1550 nm wavelength) is fed into large-core fiber/waveguide, where its power per unit area is lower than the "Fiber Fuse" threshold. The laser power flows through the fiber toward a narrowing funnel where its size is tapered to a smaller core size of fiber/waveguide. A contaminating deposition at the end of this fiber creates a "Fiber Fuse" backward (toward the laser), damaging the fiber/waveguide on its way.

The resulting damaged fiber, the "Fiber Fuse" processed scatterer, has bubbles along its core.

The "Laser Plasma" Method for Scattering Inner Core Manufacturing (Method B)

High-energy laser light (e.g., providing 30-35 dBm CW power at 1550 nm wavelength) is fed into the core of the fiber/waveguide, impinging on a partially transparent conductive layer. The layer is very thin (only a few atomic layers), and is made of an electrically conductive material, preferably a conductive metal such as rhodium, aluminum, gold, silver, chromium or nickel, or a combination or alloy of such metals.

Such thin layers of conducting materials are known to enhance the electric field strength in their vicinity due to local irregularities of their surface, where the surface irregularities induce field concentration, resulting in lower power needed to create an electrical breakdown and damage. Such thin nanometric layers may be modeled as a plurality of aggregates of nano-particles (see, e.g., M. Quinten, "Local Fields Close to the Surface of Nanoparticles and Aggregates of Nanoparticles," Appl. Phys. B 73, 245-255 (2001), and the book "Absorption and Scattering of Light by Small Particles" by C. F. Bohren and D. R. Huffmann, Wiley-Interscience (1998), Chapter 12 [showing strong field enhancement factors (up to 105) for few-nanometer particles as well as wide extinction spectra for various materials and shapes].

When the thin layer of conductive material is impinged with optical power exceeding a predetermined threshold, strong electric fields, which can lead to local electrical breakdown, are generated at certain sites in proximity to the metal surface. This leads to a visible-light-emitting arc discharge, where plasma is created. The generated plasma greatly increases the absorption of the propagating light, and the energetic discharge creates catastrophic damage at or near the metal surfaces. This damage includes cratered regions in the end surfaces of the waveguide sections on opposite sides of the conductive metal layer. Thus, the waveguide permanently becomes highly scattering. The combination of a highly scattering material and embedded absorbers creates an absorbing volume that is heated to elevated temperatures.

These two methods were tested experimentally by simulation of the hot tip and optimization of its dimensions and materials. The optimization goals were: maximal absorption and high temperature operation. The results showed over 1000° C. temperature of the hot tip, and lasted for many tens of hours absorbing 1-2 watt optical power.

BRIEF DESCRIPTION OF THE DRAWINGS

The invention will now be described in connection with certain preferred embodiments, with reference to the following illustrative figures so that it may be more fully understood. The specific figures shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings, making apparent to those skilled in the art how the several forms of the invention may be embodied in practice.

In the drawings.

DETAILED DESCRIPTION OF PREFERRED EMBODIMENTS

Figure 1:
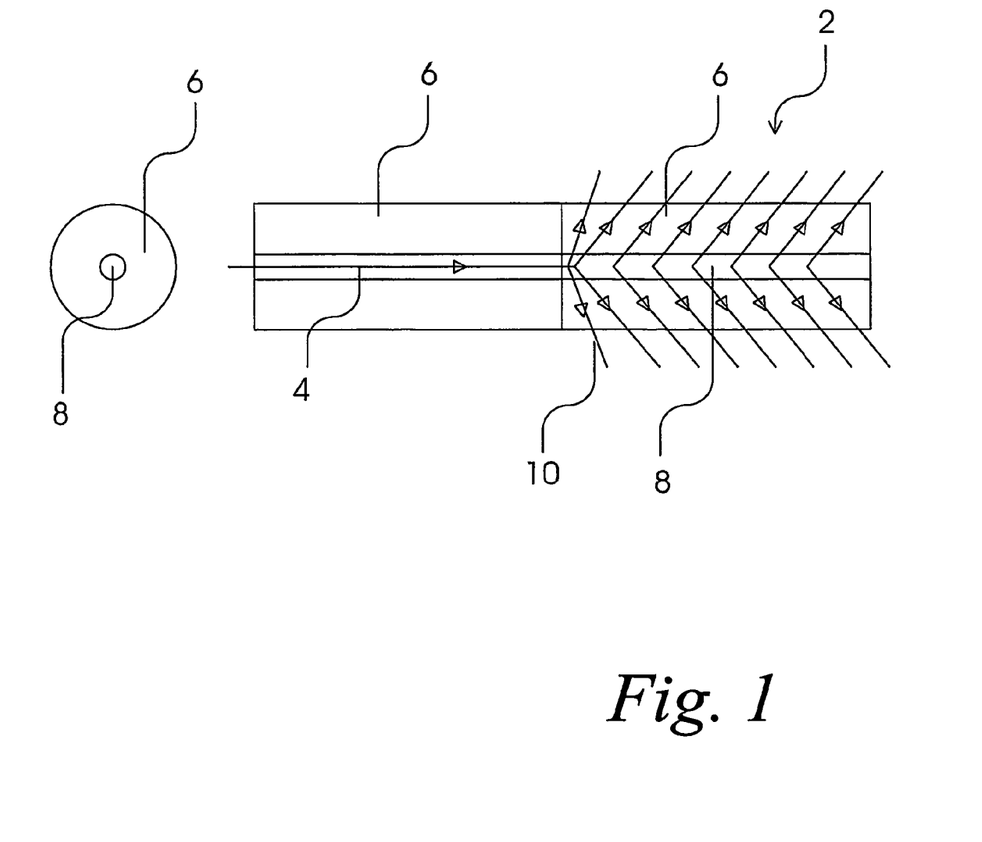
FIG. 1 is a schematic, cross-sectional view of an optical cylindrical hot tip at an end of a fiber.

Referring now to FIG. 1, there is shown an optical hot tip device 2, composed of a fiber with a core 4 and cladding 6 (e.g., a single-mode silica SMF 28 fiber). The light propagates through the core 4, affixed to an optical fiber of similar dimensions that has a scattering core 8. The fiber can be any fiber and not only the one in the example. The scattering core is produced, e.g., by the "Fiber Fuse" method. The scattered light 10 goes through the silica cladding 6 into an absorber outside. The absorber may be any optically absorbing fluid or solid. The absorber may be a black epoxy or black paint. Alternatively, the absorber may be a metal such as tantalum, molybdenum, or a combination thereof The scattered light wavelength preferably matches the absorbing medium lines in order to be absorbed efficiently.

Figure 2:
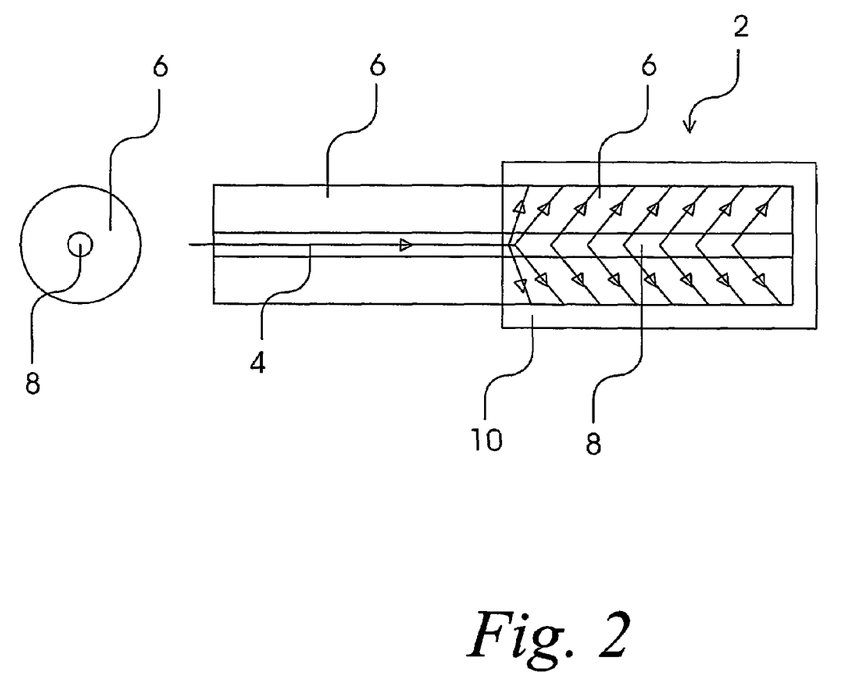
FIG. 2 is a schematic, cross-sectional view of an optical cylindrical hot tip with a heat sink at an end of a fiber.

In FIG. 2, there is shown an optical hot tip device 2 composed of a fiber with a core 4 and cladding 6 (e.g., a single-mode silica SMF 28 fiber). The light propagates through the core 4 affixed to an optical fiber of similar dimensions that has a scattering core 8 produced by the "Fiber Fuse" method. The scattered light 10 goes through the silica cladding 6 into an absorber 12, which covers the entire external area of cladding. The absorber 12 has a surface area that is about 100 times that of the surface area of the scattering core 8. The larger area of the absorber 12 allows better heat conduction outwardly. The absorber 12 should be a relatively short distance from the fiber in order to more easily conduct or convect the heat. Preferably, the absorber 12 should, at a maximum, be 100 microns away from the scattering core 8. Preferably, the absorber should be between about 50 microns and 70 microns away from the scattering core 8. The absorber 12 may be an optical black paint or epoxy paint, thus allowing for a wide range of wavelengths to be absorbed. In other embodiments, the absorber 12 includes a metal made of tantalum, molybdenum, or a combination thereof. In other embodiments, other metals may be used.

Figure 3:
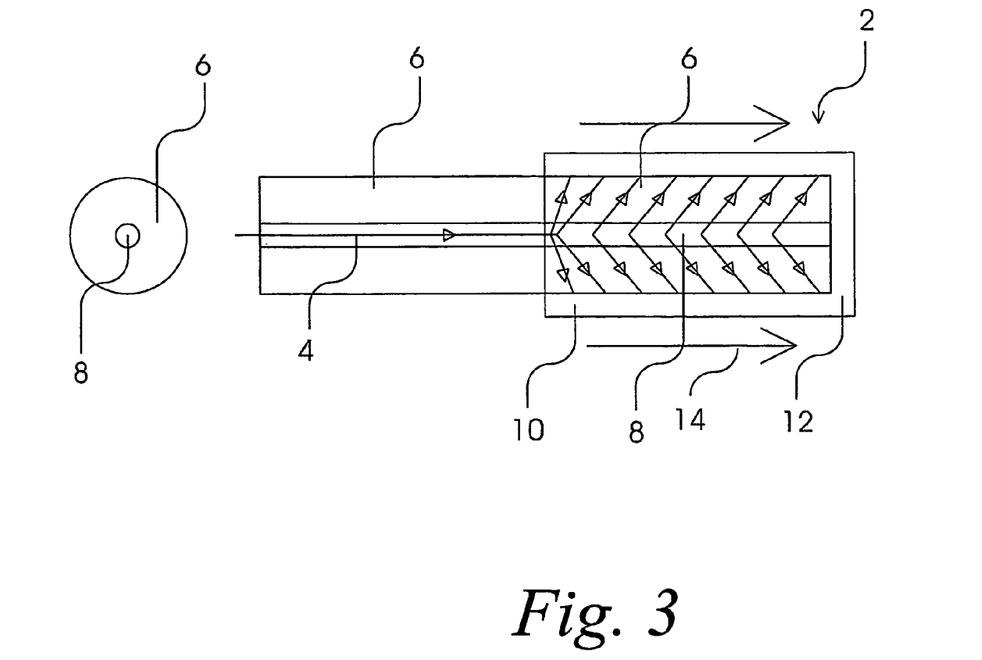
FIG. 3 is a schematic, cross-sectional view of an optical cylindrical hot tip with a heat sink at an end of a fiber, used for heating a flow of fluid along its axis.

FIG. 3 illustrates a device similar to that shown in FIG. 2. However, here the hot tip 2 is exposed to a fluid flow 14 around the tip, longitudinal or transverse, providing heat to the fluid by conduction and convection.

Figure 4:
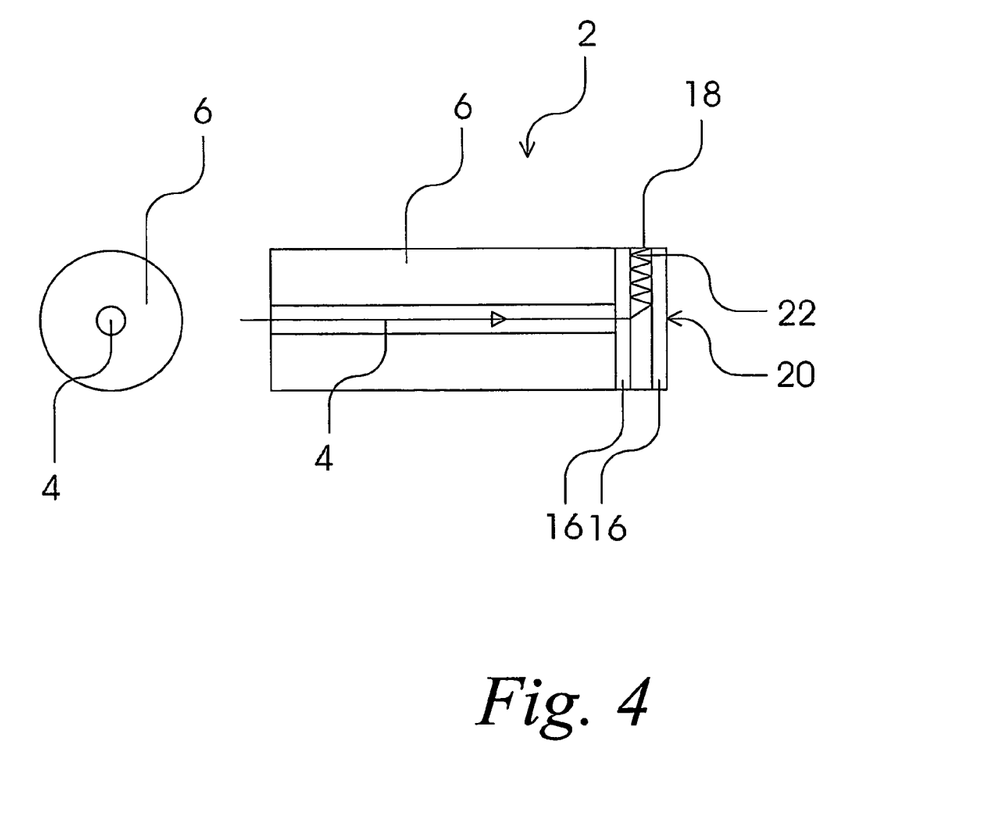
FIG. 4 is a schematic cross-section view of the laser-plasma method of hot tip production.

FIG. 4 shows a schematic cross-section of the laser-plasma method of hot tip production. Here, high-energy laser light (e.g., providing 30-35 dBm CW power at 1550 nm wavelength) from the core 4 of the fiber/waveguide impinges on a partially transparent conductive layer 16. The layer 16 is very thin (only a few atomic layers, e.g., a few nanometers), and is made of an electrically conductive material, preferably a conductive metal such as rhodium, aluminum, gold, silver, chromium or nickel, or a combination or alloy of such metals. Such thin layers of conducting material are known to enhance the electric field strength in their vicinity due to local irregularities of their surface, where the surface irregularities induce field concentration, resulting in lower power needed to create an electrical breakdown, and damage. Such thin nanometric layers may be modeled as a plurality of aggregates of nano-particles (see, e.g., M. Quinten, "Local Fields Close to the Surface of Nanoparticles and Aggregates of Nanoparticles," Appl. Phys. B 73, 245-255 (2001) and the book "Absorption and Scattering of Light by Small Particles" by C. F. Bohren and D. R. Huffmann, Wiley-Interscience (1998), Chapter 12 [showing strong field enhancement factors (up to 105) for few-nanometer particles as well as wide extinction spectra for various materials and shapes]. When the thin layer of conductive material is impinged with optical power exceeding a predetermined threshold, strong electric fields, which can lead to local electrical breakdown, are generated at certain sites in proximity to the metal surface. This leads to a visible-light-emitting arc discharge, where plasma is created. The generated plasma greatly increases the absorption of the propagating light, and the energetic discharge creates catastrophic damage at or near the metal surfaces. This damage includes cratered regions in the end surfaces of the waveguide sections on opposite sides of the conductive metal layer. Thus, the waveguide end permanently becomes highly scattering. Following the conductive layer 16 is another dielectric layer 18, and more conductive layers 16 may follow it.

The combination of a highly scattering material and embedded absorbers (either the conductive particles created by the discharge from layer 16 or artificially introduced absorbers like nano-particles of carbon) create an absorbing volume 21 that is heated to elevated temperatures. After this process is finished, the light impinging from core 4 into the absorbing volume 21 is scattered in directions 22 and is absorbed by the conductive and absorbing particles, thus heating the volume 21 to elevated temperatures over 1000° C. The hottest spot is in the symmetry point 20.

Figure 5:
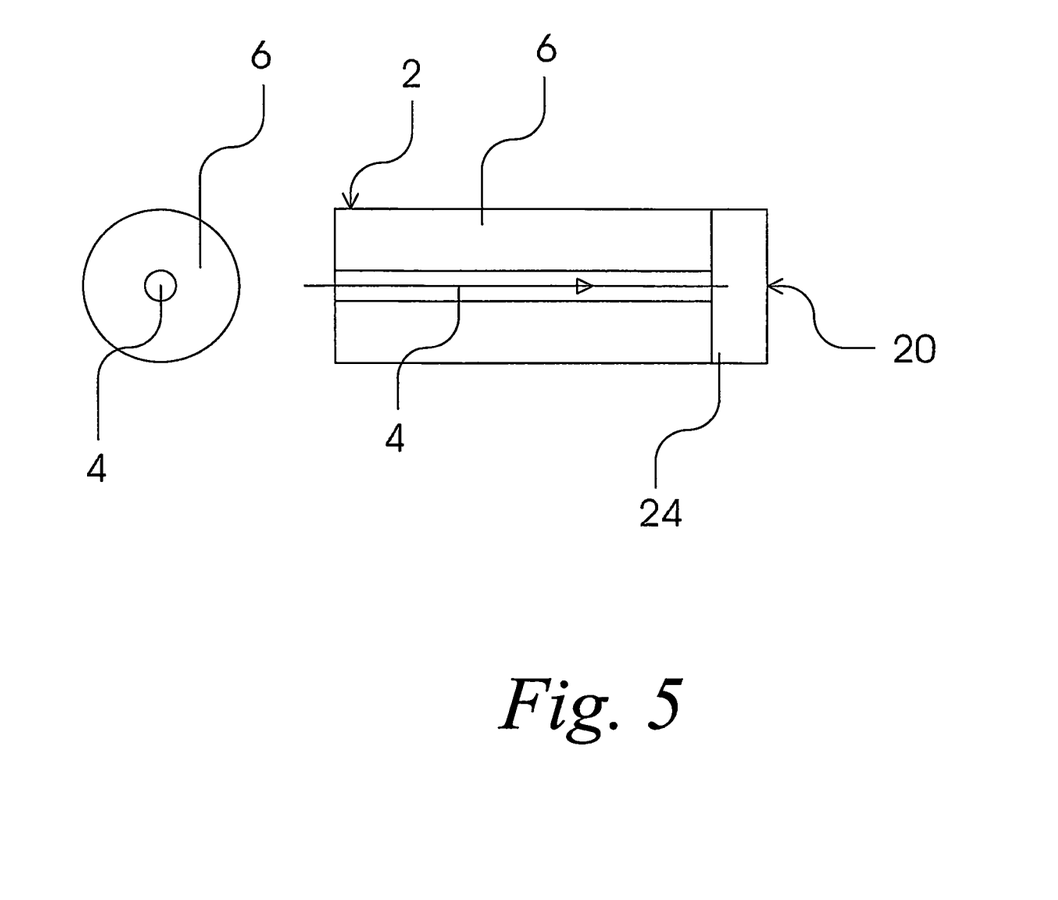
FIG. 5 is a schematic cross-section view of the laser-plasma method of hot tip production.

FIG. 5 illustrates the result of the process and method of FIG. 4, showing a highly scattering and absorbing volume 24 (that includes the conductors 16 and the dielectric layer 18) having dimensions of about 1-2 micrometers in length and a diameter of, e.g., 125 micrometers. The hottest spot is in the symmetry point 20.

Figure 6:
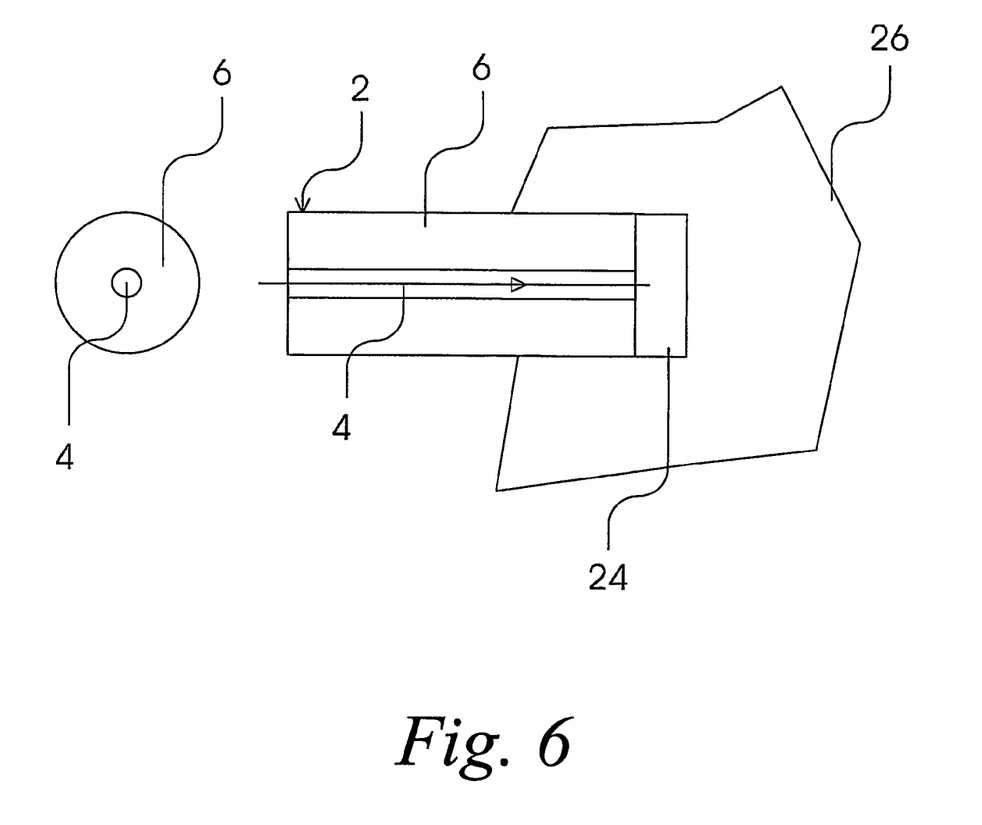
FIG. 6 is a schematic cross-section view of the laser-plasma method of hot tip production and some of its applications.

FIG. 6 illustrates some applications of the hot tip of FIGS. 1, 2, 3, 4, 5 and 7 when immersed in fluid or solid 26. The matter 26 can be, e.g., an air and fuel mixture, as in an internal combustion engine, where the hot tip 24 serves as an ignition device, optically energized and operated. The matter 26 can be, e.g., an explosive or pyrotechnic material, as in a rocket engine or an exploding device, where the hot tip 24 serves as an ignition fuse, optically energized and operated. The matter 26 can be, e.g., a living tissue to be cut in an operation, where the hot tip 24 serves as a cutting knife, optically energized and operated.

Figure 7:
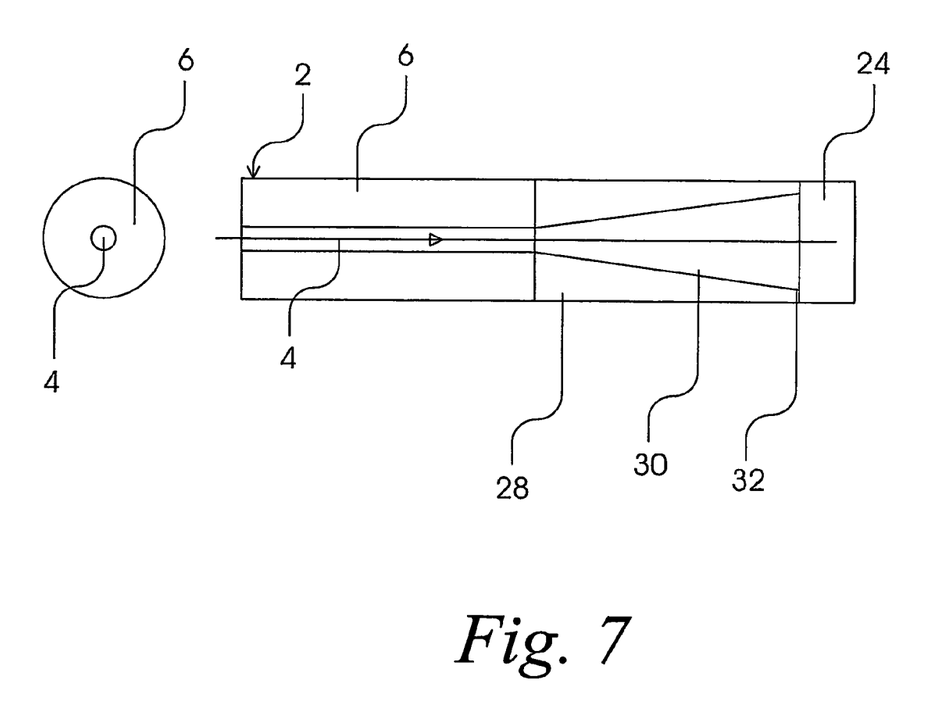
FIG. 7 is a schematic diagram of an enlarged hot tip of desirable dimensions

FIG. 7 illustrates another way to create the hot tip of FIG. 5, with a controllable area of the impinging light. Here a fiber having a constant index of refraction across 28 is coupled (e.g., by fusion splicing) to the light-conducting fiber 6. The light output, not being confined by an index step, diverges in a cone 30, reaching its maximum diameter at spot 32. In this way the light impingement diameter is controlled by the index and length of the core-less fiber 28, enabling the selection of any diameter from the core diameter (e.g., 10 micrometers) to the clad diameter (e.g., 125 micrometers or more).

It will be evident to those skilled in the art that the invention is not limited to the details of the foregoing embodiments, and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes, which come within the meaning and range of equivalency of the claims, are therefore intended to be embraced therein.

What is claimed is:

1. An optical hot tip for absorbing high optical energy traveling in a fiber or waveguide, comprising:
   a core that receives the high power optical energy; and
   a scattering end tip adjacent to an end of the fiber or waveguide and containing an absorber, such that the optical energy is impinged on the absorber to heat the absorber to a temperature of at least about 1000° C.

2. The optical hot tip of claim 1 wherein the absorber comprises a first conductive layer for scattering and absorbing the optical energy.

3. The optical hot tip of claim 1 wherein the absorber further comprises a second conductive layer and a dielectric between the first and second conductive layers.

4. The hot tip of claim 1 wherein the absorber comprises a laser-plasma type absorber.

5. The hot tip of claim 1 wherein the core comprises a conically-shaped end.

6. The optical hot tip of claim 1 wherein the absorber comprises a scattering core that receives the high power optical energy and an absorbing layer at least partially surrounding the scattering core to conduct the high power energy away from the scattering core.

7. The optical hot tip of claim 1 wherein the absorbing layer is placed at a distance of up to 100 microns from the scattering core.

8. The optical hot tip of claim 1 wherein said absorber has a surface area of approximately 100 times of the surface area of the scattering core.

9. The optical hot tip of claim 1 wherein the absorbing layer comprises at least one of tantalum and molybdenum.

10. The optical hot tip of claim 1 wherein the absorber comprises a metal.

11. The optical hot tip of claim 1 wherein said absorber is at least one metal selected from the group consisting of rhodium, aluminum, gold, silver, chromium and nickel.

12. The optical hot tip of claim 1 wherein scattering end tip is formed by a laser-plasma method.

13. An optical hot tip for absorbing high optical energy traveling in a fiber or waveguide, comprising:
   a scattering core that receives the high power optical energy; and
   an absorbing layer at least partially surrounding the scattering core to conduct the high power energy away from the scattering core, the absorbing layer being in contact with the fiber or waveguide.

14. The hot tip of claim 13 wherein the absorbing layer has a surface area of at least about 100 times of the surface area of the scattering core.

15. The hot tip of claim 13 wherein the absorbing layer heats to a temperature of at least about 100° C.

16. The hot tip of claim 13 wherein the absorbing layer heats to a temperature of at least about 1000° C.

17. The hot tip of claim 13 wherein the absorbing layer comprises at least one material selected from the group consisting of black paint, black epoxy, tantalum, molybdenum, and a combination of tantalum and molybdenum.

18. The hot tip of claim 13 wherein the scattering core is produced by a fiber fuse method.

19. An optical hot tip for absorbing high optical energy traveling in a fiber or waveguide, comprising:

a core that receives the high power optical energy; and a first conductive layer adjacent to an end of the fiber or waveguide, such that the optical energy is impinged on the first conductive layer, creating a scattering end tip.

20. The hot tip of claim 19, further comprising a second conductive layer and a dielectric layer between the first and second conductive layers.

21. The hot tip of claim 19 wherein the scattering end tip heats to a temperature of at least about 1000° C.

22. The hot tip of claim 19 wherein the first conductive layer comprises at least one metal selected from the group consisting of rhodium, aluminum, gold, silver, chromium, and nickel.

23. The hot tip of claim 19 wherein the scattering end tip is formed by a laser plasma method.

24. The hot tip of claim 19 wherein the scattering end tip is a core-less end tip.

25. A method of heating a material with the optical hot tip of claim 19, the method comprising:

disposing said hot tip and said material to be heated adjacent each other, and passing a high-power optical beam into said scattering core to heat said material.

26. The method of claim 25 wherein said material to be heated is at least one material selected from the group consisting of a fuel-air mixture, a fluid, an explosive, a pyrotechnic and live tissue.

\* \* \* \* \*